United States Patent
Malowaniec et al.

(10) Patent No.: US 7,462,754 B2
(45) Date of Patent: Dec. 9, 2008

(54) ABSORBENT STRUCTURE AND METHOD FOR PRODUCING THE SAME

(75) Inventors: Krzysztof D. Malowaniec, Heidenheim (DE); Rainer Mangold, Herbrechtingen (DE); Thomas Wurster, Heidenheim (DE)

(73) Assignee: Paul-Hartmann AG, Heidenheim (DE)

( * ) Notice: Subject to any disclaimer, the term of this patent is extended or adjusted under 35 U.S.C. 154(b) by 37 days.

(21) Appl. No.: 11/199,016

(22) Filed: Aug. 8, 2005

(65) Prior Publication Data

US 2005/0273067 A1 Dec. 8, 2005

Related U.S. Application Data

(63) Continuation of application No. 10/182,587, filed as application No. PCT/EP01/02387 on Mar. 2, 2001, now abandoned.

(30) Foreign Application Priority Data

Mar. 2, 2000 (DE) ................. 100 10 268
Mar. 2, 2000 (DE) ................. 100 10 269

(51) Int. Cl.
*A61F 13/15* (2006.01)
*A61F 13/20* (2006.01)
*C08J 9/00* (2006.01)

(52) U.S. Cl. ............. 604/369; 521/50; 604/385.01

(58) Field of Classification Search ......... 521/131–140, 521/179; 156/244.11; 604/367–370; 525/63; 264/330; 428/375
See application file for complete search history.

(56) References Cited

U.S. PATENT DOCUMENTS

| | | | |
|---|---|---|---|
| 3,940,467 A * | 2/1976 | Brachman | .......... 264/45.5 |
| 4,690,679 A * | 9/1987 | Mattingly et al. | .......... 604/383 |
| 4,977,211 A * | 12/1990 | Doi et al. | .......... 525/54.31 |
| 5,061,259 A | 10/1991 | Goldman et al. | |
| 5,076,774 A | 12/1991 | Farrington et al. | |
| 5,308,346 A | 5/1994 | Sneller et al. | |
| 5,439,458 A | 8/1995 | Noel et al. | |
| 5,451,452 A * | 9/1995 | Phan et al. | .......... 442/374 |
| 5,705,536 A * | 1/1998 | Tomka | .......... 521/84.1 |
| 5,859,077 A | 1/1999 | Reichman et al. | |
| 5,961,763 A | 10/1999 | Makoul et al. | |
| 6,019,871 A | 2/2000 | Rökman et al. | |
| 6,071,580 A | 6/2000 | Bland et al. | |
| 6,214,274 B1 | 4/2001 | Melius et al. | |
| 6,534,572 B1 | 3/2003 | Ahmed et al. | |
| 2003/0012928 A1 | 1/2003 | Malowanlec et al. | |

(Continued)

FOREIGN PATENT DOCUMENTS

DE 2 222 780 5/1972

(Continued)

*Primary Examiner*—Tatyana Zalukaeva
*Assistant Examiner*—Melanie J Hand
(74) *Attorney, Agent, or Firm*—YoungBasile

(57) ABSTRACT

A method for producing an absorbent structure and the resulting absorbent structure. The method includes the steps of introducing a thermoplastic polymer into an extrusion apparatus, melting the thermoplastic polymer material having a moisture content of at least 0.5 percent by weight into the extrusion apparatus, and extruding the mixture such that the fluid in the superabsorbent polymer material evaporates as pressure is released and induces foaming of the thermoplastic polymer that bonds the particulate polymer material together to create a matrix.

10 Claims, 6 Drawing Sheets

| U.S. PATENT DOCUMENTS | | | JP | 04136045 | 9/1990 |
|---|---|---|---|---|---|
| 2003/0040729 A1 | 2/2003 | Malowanlec et al. | WO | WO 94/13460 | 6/1994 |
| | | | WO | WO 98/56430 | 12/1998 |

FOREIGN PATENT DOCUMENTS

| JP | 9026246 | 8/1982 |
|---|---|---|

* cited by examiner

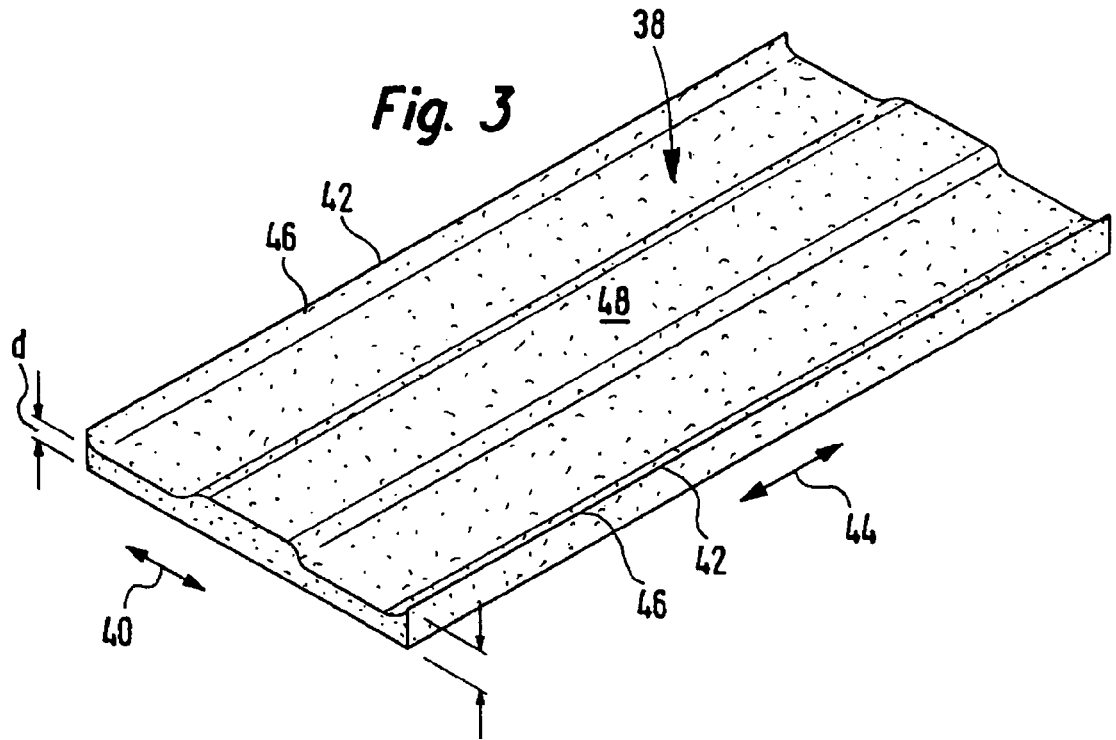
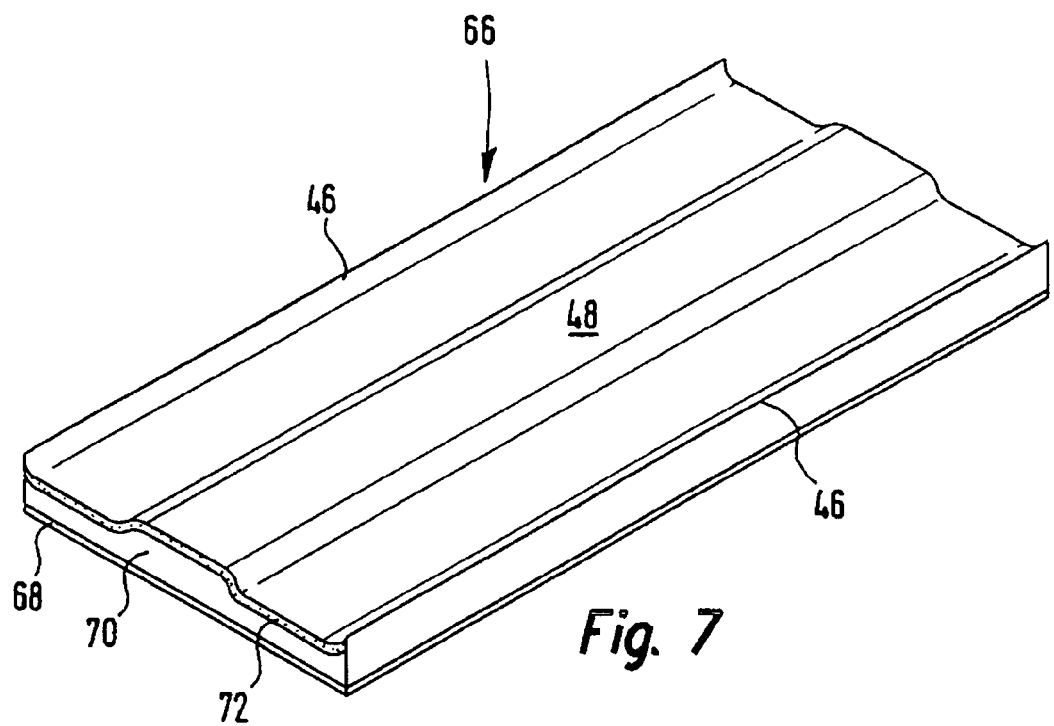

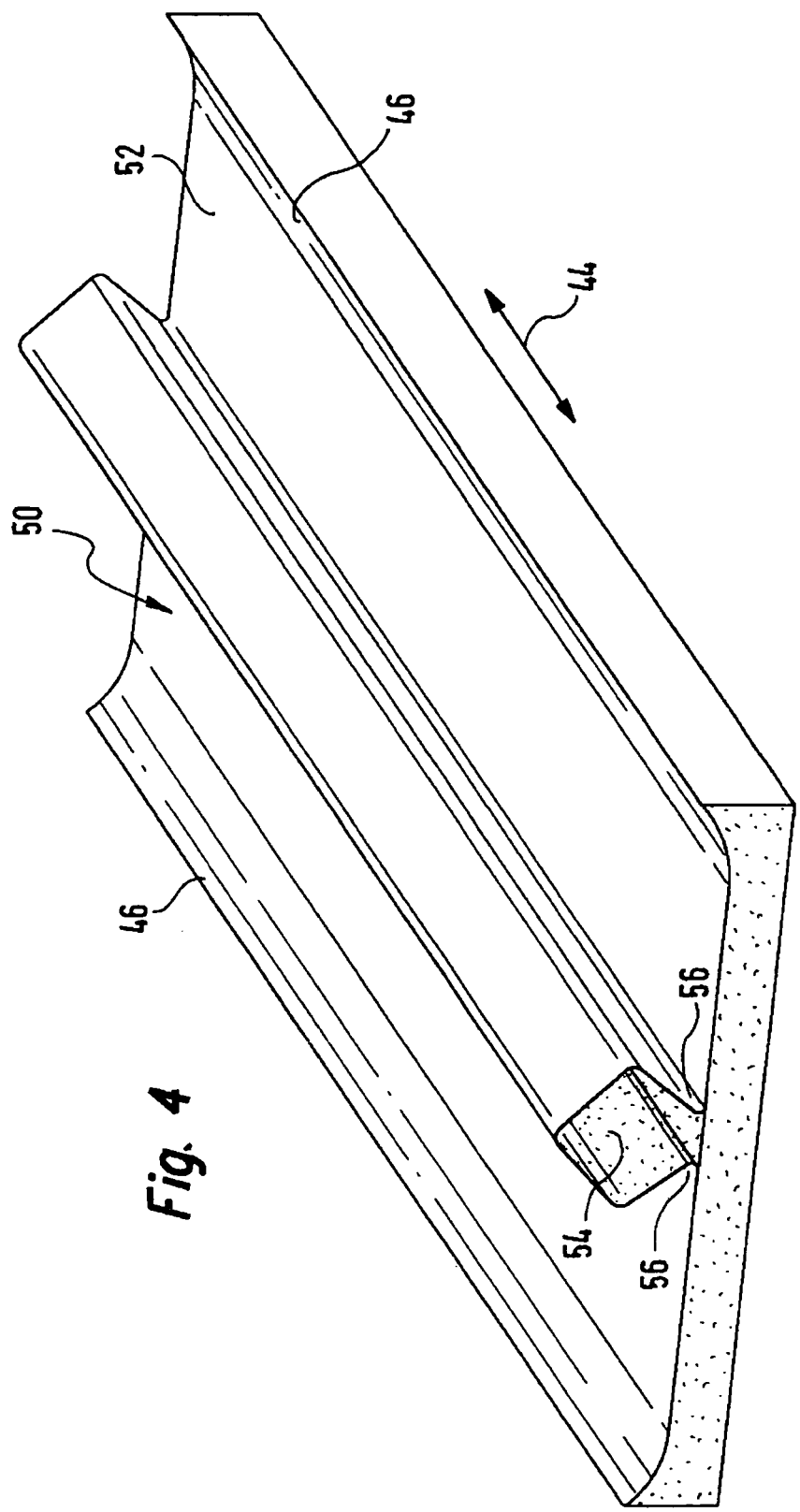

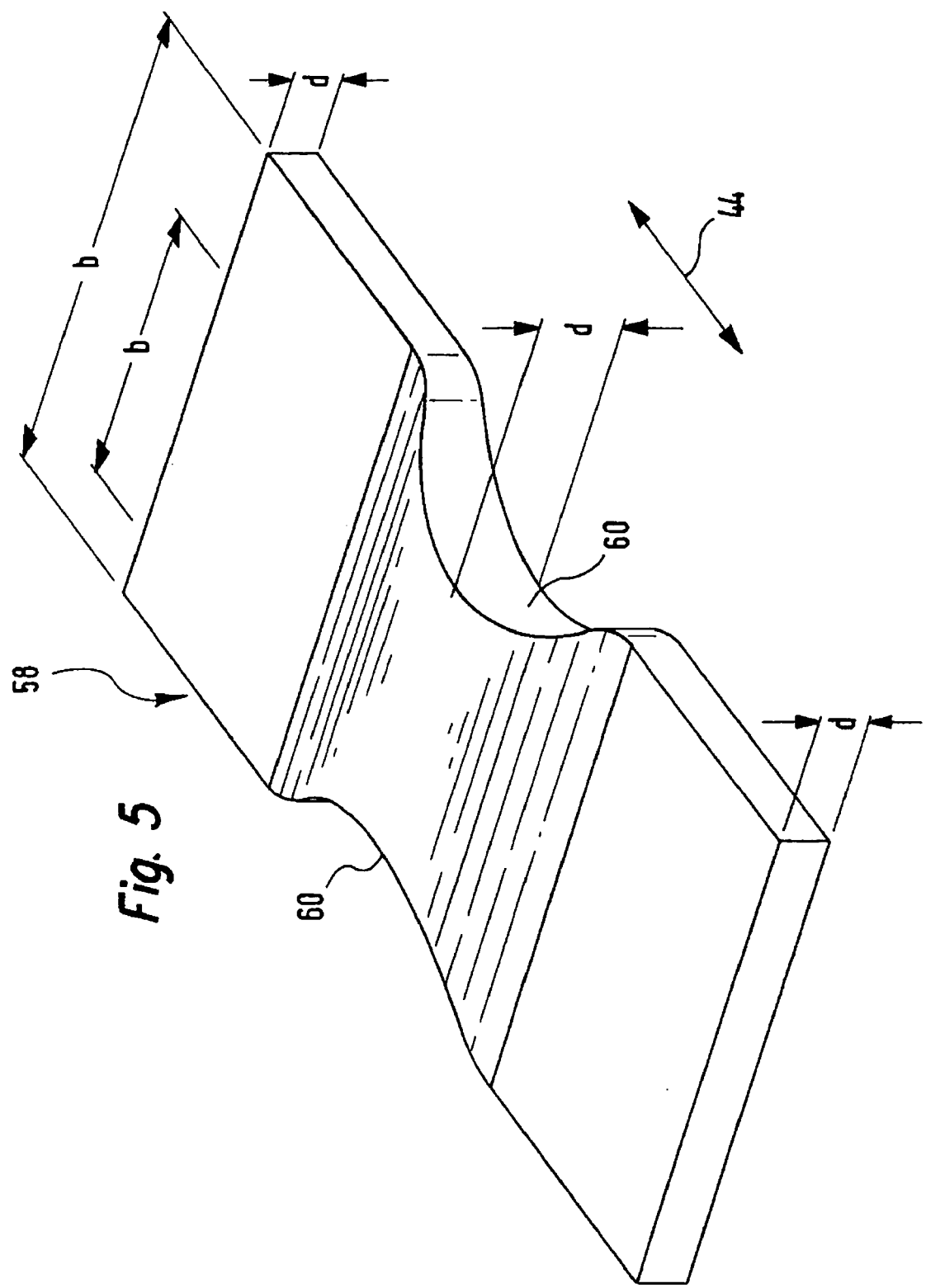

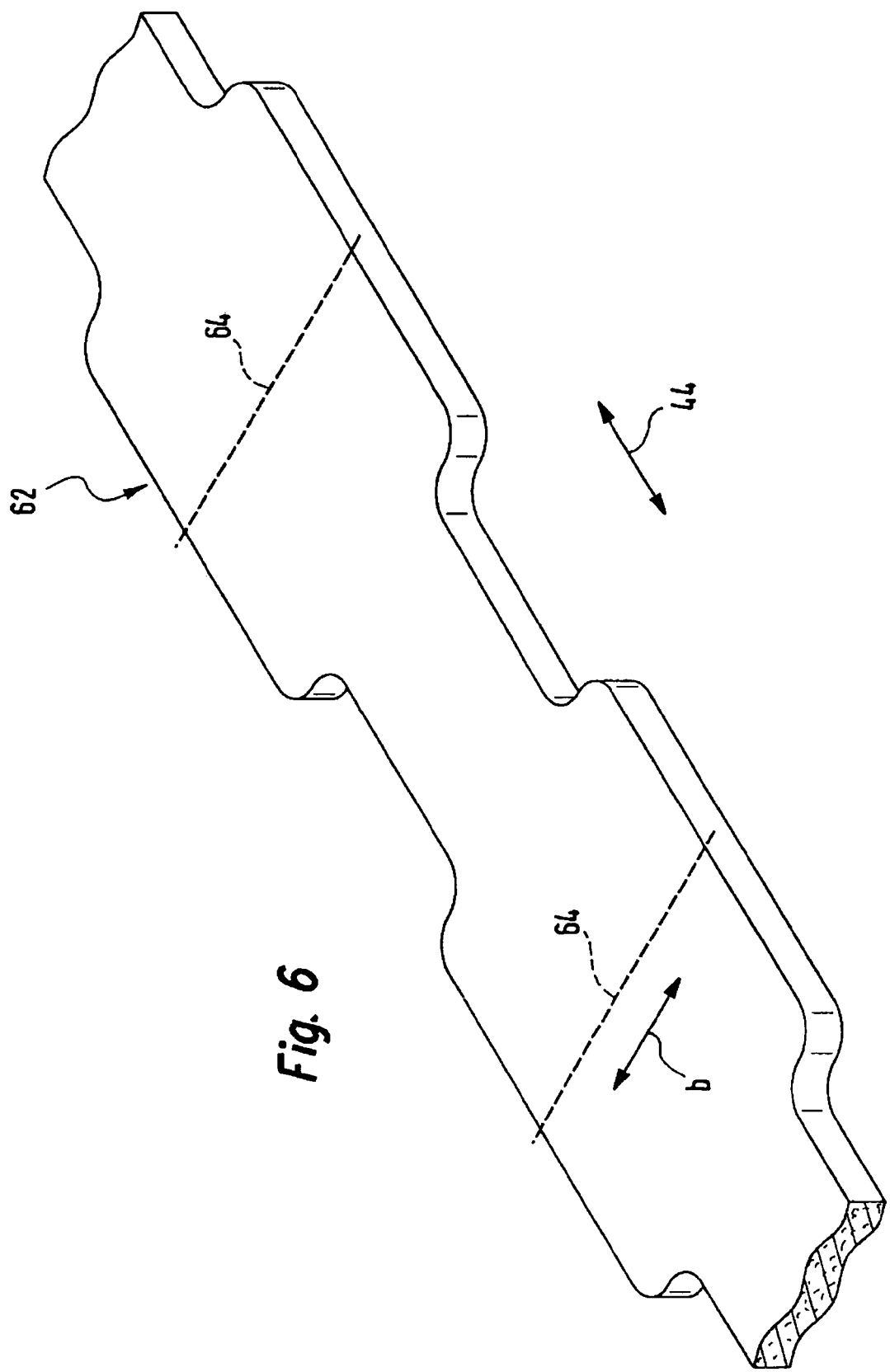

ABSORBENT STRUCTURE AND METHOD FOR PRODUCING THE SAME

This application is a continuation of U.S. Ser. No. 10/182,587 filed Jul. 31, 2002, now pending, which is a national stage filing of International Application PCT/EP01/02387 filed Mar. 2, 2001, which claims priority from German Application No. 100 10 269.7, filed Mar. 2, 2000, and German Application No. 100 10 268.9, filed Mar. 2, 2000.

BACKGROUND

The invention relates to an absorbent structure formed on the basis of particulate, superabsorbent polymer materials, where the superabsorbent polymer materials are bonded together by a lower-melting thermoplastic polymer. The invention relates furthermore to a method for producing an absorbent structure of this kind and a hygiene article having such an absorbent structure as an absorbent core layer.

When an absorbent structure on the basis of superabsorbent polymer materials is mentioned, this is understood to mean a structure having an amount of more than 70% by weight of superabsorbent polymer materials. It is in line with established understanding and established practice in the sphere of interest here of absorbent structures that superabsorbent materials are meant to refer to such materials which by absorption or gel formation are able to absorb and permanently retain at least about ten times their own mass in fluid. The fluid is bonded into the molecular structure of these materials and not simply absorbed into pores in the materials, from which it could be squeezed out again. Current superabsorbent materials are water-insoluble, cross-linked polymers which are capable of absorbing aqueous fluids and body exudates such as urine or blood by swelling and forming hydrogels and permanently retaining the quantity of fluid absorbed at least under a certain surrounding pressure.

It has been shown that absorbent core structures with such a high content, more than 70% by weight, of superabsorbent polymer materials (SAP) cannot be realized using traditional fiber-based structures, because the particulate SAP materials cannot be arranged to be sufficiently accessible on the one hand and not be sufficiently immobilized on the other hand.

From DE-A-2 222 780 it is known to apply the particulate superabsorbent polymer materials on an underlayer together with particles of a thermoplastic material to produce an absorbent structure formed on the basis of superabsorbent polymer materials and then to melt the thermoplastic material to obtain a composite.

A structure of this type of superabsorbent polymer materials and thermoplastic polymers was not successful in practice, because the accessibility of the superabsorbent materials for the impinging fluid was not sufficiently ensured. Moreover, this structure proved to be too rigid and was consequently characterized by insufficient comfort for the wearer.

The production of an open-cell polypropylene foam with a pore content of more than 20% by volume is known from WO 94/13460. Packaging and the use of the foam for sound absorption and thermal insulation are named as areas of application.

The production of an extruded thermoplastic foam is also known from WO 98/56430. The foam preferably has a structure consisting of cell walls and cavities. The foam can be used, according to the description, as the container for a piece of meat or a layer in a diaper.

The object of the invention is to eliminate the aforementioned disadvantages in the case of an absorbent structure of the generic type named at the beginning having a high SAP content, that is, to achieve a flexible structure having good fluid absorption and retention characteristics, which can also be manufactured simply.

SUMMARY

This object is achieved by a conventional absorbent structure which under the invention is manufactured by extruding the thermoplastic polymer and superabsorbent particulate polymer materials having a moisture content of at least 0.5% by weight relative to the total mass of the superabsorbent polymer materials and evaporating the fluid in the superabsorbent polymer materials and thereby inducing foaming in the structure.

With the present invention the proposal is made to bond granular, particulate superabsorbent polymer material by means of at least partially molten thermoplastic polymer materials by extruding the mixture which is subject to pressure and temperature in the presence of a blowing agent which is formed from the moisture content of the superabsorbent materials. It is hereby possible on the one hand to immobilize, that is, fix in position the particulate superabsorbent polymer materials within the structure and, on the other, a structure is formed which can be extremely well penetrated by an impinging fluid, such as urine for example. It was shown that the fluid can penetrate very quickly into the open-pore foamed structure formed through extrusion of the mixture under expansion of the blowing agent, meaning evaporation of the fluid contained in the superabsorbent polymer materials, and can reach the superabsorbent polymer materials contained therein where it is then permanently retained. It also turned out that the swellable, superabsorbent polymer materials in the structure under the invention to a far lesser degree cause the so-called gel blocking effect which proves to be problematic with higher weight percentages of swellable polymer materials in absorbent fiber structures because the polymer materials swelling in the fluid compress the interstices between fibers so that no capillarity is left to carry the fluid into still unutilized absorbent core areas. An additional problem in the cases of absorbent structures formed from natural fibers is their tendency to collapse in a saturated condition, which problem is also described as wet collapse. This also leads to a reduction of the ability to distribute fluid within an absorbent structure. In the case of the extruded absorbent structure under the invention, the problems discussed in what preceded do not occur or to a far lesser degree, for which reason the absorption capability of the superabsorbent polymer materials is available almost in its entirety to absorb the impinging fluid even at very high concentrations of more than 70% by weight.

By using the moisture content, that is, the fluid which constitutes the at least 0.5% by weight moisture of the superabsorbent polymer material, as the blowing agent during the extrusion of the mixture of superabsorbent polymer materials and thermoplastic polymer a critical effect is achieved for the absorption capability of the superabsorbent polymer materials in the finished structure: As a result of the abrupt evaporation of the fluid out of the particulate superabsorbent polymer materials during extrusion, the surface of these particles and the thermoplastic polymer settling on the surface of the particles is torn open in all directions. This tearing open creates outstanding accessibility of the particulate superabsorbent polymer materials, and it prevents the molten thermoplastic polymer from settling like a melt over the surface of the particles and thus obstructing the ingress of fluid. As a result of this inventive measure, namely to use moist superabsorbent polymer materials for the extrusion process, the accessibility of the particulate superabsorbent polymer materials to fluid could be further improved.

The size of the particles of superabsorbent polymer materials is in the normal range and the mass median is preferably about 200-800 microns, where preferably no more than 20% by mass of the particles are smaller than 200 microns; in this respect reference is made to the disclosure in U.S. Pat. No. 5,061,259.

Preferably the inventive absorbent structure is manufactured using a superabsorbent polymer material having a moisture content of at least 1% by weight and especially preferably of at least 4% by weight. It is clear that moisture content as high as possible is striven for, whereby this is limited by the increasingly poor manageability of the particulate superabsorbent polymer materials as the moisture content increases. The invention also does not preclude that, in addition to the use of superabsorbent polymer materials with a moisture content in the range quoted, a blowing agent, in the form of $CO_2$ for example, is additionally used. However, surprisingly as it turned out, this is not necessary to obtain adequate fluid retention capacities for the applications.

The extruded open-pored structure exhibits a retention capacity of at least 10 g fluid per gram of the extruded structure. Absorption capacity can be determined in a test procedure to be described in greater detail.

In a further development of the invention, the percentage by mass of the thermoplastic polymer is less than 30% by weight, specifically 20% by weight, and specifically less than 10% by weight of the absorbent structure.

A polymer from the group of polyolefins, specifically polypropylenes and/or polyethylenes, has proved in a particularly preferred way to be the thermoplastic polymer which quasi forms the binding agent for the superabsorbent particulate polymer materials. Corresponding copolymers, specifically ethylene vinyl acetate copolymers, as well as halogenated polyolefins can be used. Basically, however, other thermoplastic polymers are suitable for the manufacture of the inventive absorbent structure, for example, those from the group of styrene polymers.

In order to make available a greatest possible fluid absorption volume and to expose a greatest possible surface of the superabsorbent polymer materials for fluid absorption, the degree of foaming is at least 20%, preferably it is higher, specifically 20%-50% or beyond. The degree of foaming, or the term "foaming" of the structure respectively, is defined or is understood as the increase in volume of a mass unit of the mixture in a state inside the extrusion apparatus on the one hand, or in the extruded state of the finished structure on the other hand.

In an advantageous manner the absorbent structure can comprise between 3% and 20%, preferably between 5% and 10% by weight fibers as additives. They can be natural or synthetic fibers, preferably polyester fibers, but whose melting or degradation temperature is higher than the melting temperature of the related thermoplastic polymer inside the extrusion apparatus. The effect of the fibers is that during the extrusion process passages are formed which promote the penetration of aqueous fluid into the structure.

In a particularly advantageous way the invention allows absorbent structures to be formed whose basic weight varies in the longitudinal direction and/or in the transverse direction of the structure, where the longitudinal direction corresponds to the direction of extrusion. By means of suitably shaping an extrusion opening, specifically an extrusion slit, any kind of cross-sectional structures can be achieved. Thus, viewed particularly in cross-section perpendicular to the longitudinal direction, the thickness of the absorbent structure could be greater in the center and corresponding to the structure of the extrusion opening could decrease in any manner at all to the sides.

Like all the absorbent structure to be explained in what follows, the structure can comprise in addition a surfactant substance, specifically a hydrophilizing agent in an amount of preferably 0.2%-10%. The already extruded structure can be secondarily impacted with the hydrophilizing agent. Preferably this agent is fed to the extruder together with the remaining initial materials or injected into the already molten polymer mass, so it is already present commingled with the polymer melt before it is extruded.

Advantageously alkyl sulfonates, fatty acid derivatives or fluorine chemicals are used for this—as described in the publication "Polymer Melt Additives: Their Chemistry, Structure and Uses," (authors Gasper et al., lecture during Insight 1999—Nonwovens Business/Fiber & Fabric Conferences, San Diego, Calif., 1-2 Nov., 1999. Proceedings published by Marketing Technology Services, Inc.).

Protection is also sought with this invention for a disposable, absorbent hygiene article, specifically a diaper, sanitary napkin or an incontinence pad, having a specifically multi-layer absorbent core which is characterized by an absorbent core layer of an absorbent structure of the previously described inventive type.

This absorbent core layer can be located on the side of a fluid distribution and intermediate retention layer facing outwardly from the body. It is also conceivable that the fluid distribution and intermediate retention layer which comprises fewer or no superabsorbent polymer materials, is also manufactured as an extruded, foamed structure, specifically with the addition of a blowing agent, such as $CO_2$. In this case both absorbent cores could be produced inside the manufacturing machinery by extrusion and be placed one on top of the other to create the composite layer. Direct coextrusion of both layers, i.e. production by the same extrusion apparatus, is conceivable and advantageous.

It is furthermore additionally possible to configure the inventive SAP-containing structure itself in multiple layers. For example, a first layer facing outwardly from the body can be overlaid by a second body-facing layer. In such a case, the absorbent SAP-containing structure can, for example, be furnished with an advantageous SAP profile. In particular, the first layer facing outwardly from the body can contain less SAP (in percent by weight relative to the first layer) than the second body-facing layer. It can be advantageous that the surface extent, that is the width and/or length, of the first layer facing outwardly from the body is different from the surface extent of the second body-facing layer, specifically it can be advantageous to configure the first layer facing outwardly from the body larger, specifically wider with respect to its surface extent than the second body-facing/contacting layer. This multi-layer construction of the absorbent SAP-containing structure itself can be produced simply, by direct coextrusion of the layers.

Furthermore, it would be conceivable that a fluid non-pervious layer facing outwardly from the body which is normally formed of a pre-manufactured plastic film, is produced by coextrusion with the absorbent core. In this case it would prove to be advantageous and expedient to configure all three aforementioned layers, or even additional layers by coextrusion by means of a single coextrusion apparatus inside the manufacturing machinery. A fixative means, such as a hot melt adhesive for example, can then be advantageously omitted, since the extruded layers can be fixed in position among themselves but also with respect to additional layers and/or elements in the course of their manufacture.

It is generally noted that the fluid distribution and intermediate retention layer, which can contain very little or even no superabsorbent polymer materials, can be additionally configured and manufactured in the same way as the inventive absorbent structure or the aforementioned absorbent core. It can have additives in the form of fibers or surfactant substances and be configured manufactured with a varying thickness or varying basic weight respectively.

As already mentioned in what preceded, it can prove to be advantageous if the absorbent core has a varying thickness in the longitudinal direction of the article or in the transverse direction, that is, if it is configured with a profiled shape. Through an agglomeration of material in a central area of the hygiene article, the fluid absorption capacity available there can consequently be configured with any profile in and of itself, specifically bell-curve shaped or graduated.

In an especially advantageous embodiment of the invention it is also possible that the absorbent core has upwardly extending wall sections on both sides running in the longitudinal direction of the article and toward the wearer which form a leakage barrier. These wall sections assume the function of gatherings extending upwardly in the direction of the wearer which are normally formed in known hygiene articles from nonwoven materials with inserted means of elastification.

Of course wall sections of this kind can also run in the transverse direction and can also exercise a blocking effect there, particularly for separating solid and liquid body excretions.

The present invention is also a method for producing an absorbent structure, using the following process steps:

introducing a thermoplastic polymer into an extrusion apparatus, introducing a superabsorbent particulate polymer material with a moisture content of at least 0.5%, specifically at least 1% by weight, and more specifically of at least 4% by weight, into the extrusion apparatus, melting the thermoplastic polymer material at temperatures below a melting or degradation temperature for the superabsorbent polymer material, and extruding the mixture, where the fluid in the superabsorbent polymer material evaporates as pressure is reduced and results in foaming of the thermoplastic polymer, which bonds the particulate polymer materials together to form a matrix.

The moisture contained in the superabsorbent polymer materials is thus used as a blowing agent during extrusion. The use of an additional blowing agent, such as $CO_2$ would also be conceivable, although this is not necessary. Saturated, unsaturated, cyclic hydrocarbons and halogenated hydrocarbons and noble gases such as argon, helium or nitrogen or a water/air mixture would also be conceivable.

Inside the extrusion apparatus sufficient overpressure is developed so that the fluid from the moist superabsorbent polymer materials, which is used as the blowing agent during extrusion, evaporates when they are passed through the extrusion opening.

If $CO_2$ is used as an additional blowing agent, it is introduced in the so-called supercritical state at temperatures above about 31° C. and pressures above about 73.5 bar. In this state the blowing agent can be optimally mixed to prepare a physical foaming process with the superabsorbent polymer materials and with the molten thermoplastic polymer. If this mixture is then passed through an extrusion opening into an area of lower pressure, the blowing agent evaporates with decreasing temperature, and the foamed open-pore structure is created through an increase in volume.

But since not only sufficient pressure for the fluid, or respectively the moisture in the superabsorbent polymer materials, or respectively for the blowing agent, has to be attained, but the thermoplastic polymer must be at least partially melted, temperatures of 80° C. to 200° C. are created inside the extrusion apparatus.

The extrusion cross-section is changed during extrusion to produce varying thickness or shape in the longitudinal or transverse direction of the structure being produced. If a large quantity of correspondingly configured structures is to be extruded, it proves to be advantageous if the extrusion cross-section is changed in a correspondingly oscillating fashion. This takes place transversely to the direction of extrusion, specifically in the discharge direction, whereby the thickness of an extruded web is varied, or transversely to the discharge direction, whereby its width is varied.

In order to increase the accessibility of the extruded structure for aqueous fluids, it is advantageous to expose the extruded structure to additional mechanical treatment, for example, stretching, compressing (rolling) and/or perforation by means of a fine needling tool.

Multistage rolling of the extruded structure is particularly advantageous. Multistage rolling enables the application of several temperature and/or pressure stages. In this way the extruded structure can be changed/optimized more selectively with respect to the requirements of its later use. Thus it has proved to be advantageous to compress the extruded structure in a first calendering stage at a temperature which is suitable for maintaining the thermoplastic polymer in the extruded structure above its softening point. Depending on the polymer employed, a temperature in the calendering stage of 40° C.-90° C., specifically 50° C.-60° C., has been shown to be suitable. Afterwards the extruded absorbent structure can be compressed advantageously cold in a second calendering stage, which is performed specifically at temperatures of 0° C.-30° C., specifically at 15° C.-25° C.

It has furthermore proved to be advantageous to subject the extruded structure to additional stretching.

It proves to quite particularly advantageous if the inventive method is integrated into a production process for hygiene articles and thereby an absorbent core is extruded directly inside a machine. In such an event, fiber forming and discharge stations can be dispensed with in the manufacturing machinery (at least for the extruded absorbent core). As already mentioned, several absorbent cores which are to be positioned one above the other can be produced in the same machinery.

BRIEF DESCRIPTION OF THE DRAWING

Additional details, features and benefits of the invention can be found in the appended patent claims and from the drawing and the description which follows of a manufacturing apparatus, of the manufacturing process, as well as of several embodiments of inventive absorbent structures. In the drawing:

FIGS. 2 to 6 show perspective views of different embodiments of inventive absorbent structures;

FIG. 7 shows a perspective view of an additional embodiment of a multilayer inventive absorbent structure.

DETAILED DESCRIPTION

Figure 1:
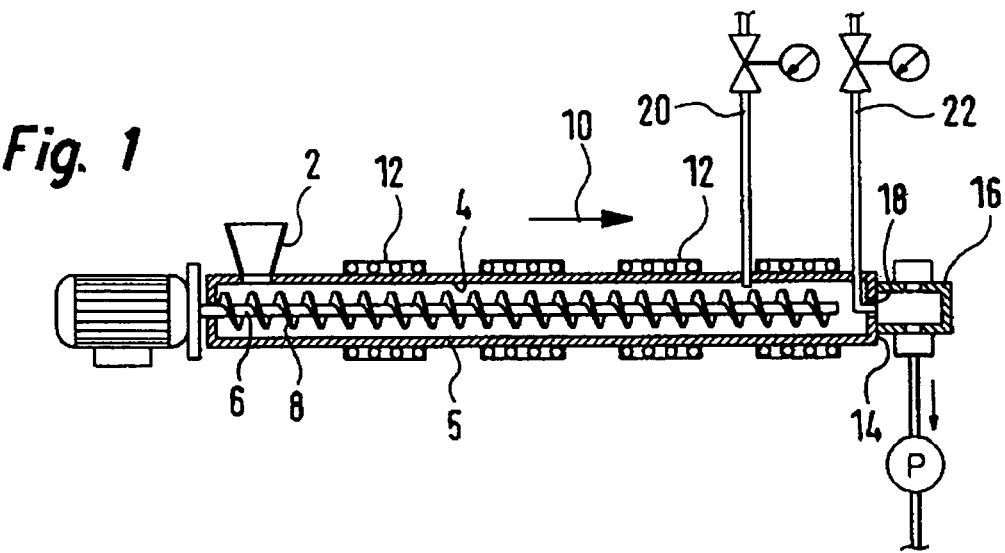
FIG. 1 shows a schematic view of an apparatus for producing an inventive absorbent structure.

FIG. 1 shows an apparatus for producing an inventive absorbent structure. The apparatus comprises a funnel-shaped feed mechanism 2 through which a solid matter mixture, which preferably was produced in advance in accordance with the by-weight percentile composition of the individual components, can be fed into a cylindrical interior 4 of a high-pressure stable tubular housing 5 of the production apparatus. A shaft 6 extends in this interior 4 having a helical screw 8 driven by an electric motor 6. When the shaft 6 is driven, the solid matter mixture which was introduced is further mixed and transported in longitudinal direction 10. Heating devices 12 are provided on the outer circumference of the tubular housing 5.

An extrusion tool 16 can be mounted on the face of the tubular housing 5 at the end opposite the feed device 2. The extrusion tool 16 communicates through an opening 18 on the face 14 with the interior 4 of the tubular housing.

Injection devices 20, 22 discharge into the interior 4, whereby they discharge quasi inside the opening 18. A blowing agent under operating pressure can be introduced into the interior 4 through the injection devices 20, 22. In this way an operating pressure can be set and maintained in the interior 4 during the extrusion process, depending on the blowing agent employed in the extrusion process, generally above 70 bar. Even without introducing an external blowing agent, operating pressure can be exerted on the mixture inside the apparatus by providing piston means or moveable wall sections.

To produce an inventive absorbent structure, a polyolefin, specifically a polypropylene and/or polyethylene granulate, can be used as an example of a thermoplastic polymer. This granulate is mixed with swellable superabsorbent polymer materials, which are adequately known in combination with absorbent layers in hygiene articles and therefore do not need to be described in greater detail, whereby these superabsorbent polymer materials have a moisture content of at least 0.5% by weight. The mixture obtained in this way is transported into the interior 4 by means of the conveying device 2. The mixture is brought up to an operating temperature by the heating devices 12 such that the thermoplastic polymer melts, but the particulate superabsorbent polymer materials are not affected in the slightest.

An operating pressure is created in the interior 4 which is suitable for extruding the partially molten mixture by means of the extrusion tool 16 using water as the blowing agent.

If an additional blowing agent, for example, $CO_2$ is to be used, it can be introduced into the interior 4 by means of the aforementioned injection devices 20, 22 in the preferably supercritical state.

When the mixture obtained in this way passes through the extrusion opening of the extrusion tool 16, the fluid contained in the superabsorbent materials evaporates as result of the accompanying drop in pressure, along with any required additional blowing agent, and the mixture is foamed, that is to say, pores or cavities which communicate with each other are formed by the expanding, evaporating fluid. The particulate superabsorbent polymer materials are fixed in place inside this cavity structure formed by the hardening of the thermoplastic polymer. They are immobilized, but thereby their surface is exposed as a result of the expansion and escape of the moisture and the subsequently created cavities and is available to absorb fluid.

Figure 2:
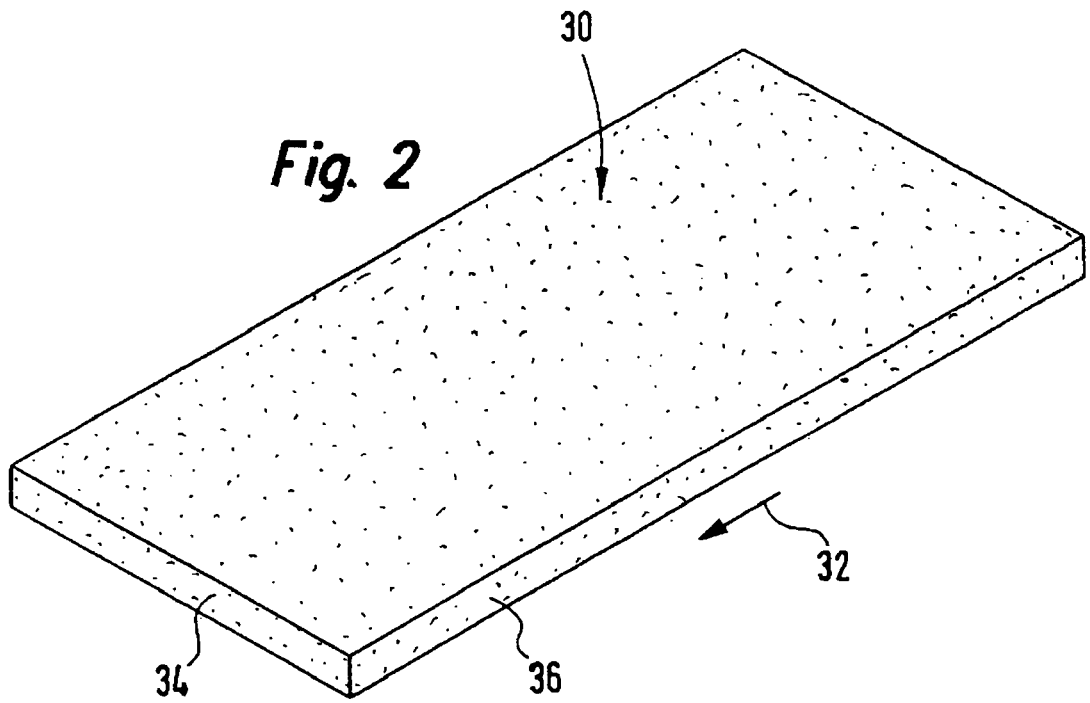

FIG. 2 shows a section of an extruded absorbent structure 30 which comprises 80% by weight a superabsorbent polymer material with a moisture content of at least 1% by weight (with respect to the mass of the superabsorbent polymer material) and 13% by weight a thermoplastic polymer, i.e. polyethylene (PE), and additionally 7% by weight polyester fibers (PES).

The extrusion device is identified with the arrow 32 so that the end surface identified with the reference numeral 34 represents the plane perpendicular to the extrusion device 32. The absorbent structure 30 is shown exactly rectangular in FIG. 2; it must be pointed out that only a basically plane surface can be obtained by an extrusion process, and that even with a precisely rectangular extrusion opening rounded edges can be formed. However it would be possible to configure a continuous web in the extrusion device 32 by lengthwise and crosswise trimming with end surfaces 34 and longitudinal surfaces 36 exactly perpendicular to each other.

FIG. 3 shows an absorbent structure 38 which has a varying thickness d in the transverse direction 40. Running along both of its longitudinal edges 42 in the longitudinal direction 44 the structure has a wall area 46 extending upwardly, that is in the thickness direction, which terminates in a point in the upward direction. From outside to inside, in the transverse direction 40, this wall area 46 falls off asymptotically and transitions into a plane section with constant thickness d and then rises again toward the center in accordance with the profile seen in FIG. 3 to a section 48 of greater thickness. A cross-sectional structure of this kind can be produced by shaping the extrusion slot correspondingly.

FIG. 4 shows a further embodiment of an inventive absorbent structure 50 having upwardly extending wall areas 46 on both sides running in the longitudinal direction 44 just as in FIG. 3. The structure 50 has an area in the center also running in the longitudinal direction 44 essentially lozenge-shaped in cross-section and rising above a surface 52. Because of its lozenge-shaped cross-section the area 54 forms undercuts 56 viewed in the direction perpendicular to the surface 52. The creation of structures which are round, elliptical or polygonal in cross section, with or without undercuts, would be conceivable. Such absorbent core structures are intended for use in female hygiene products. The raised area 54, whatever geometric form it may have, can extend at least partially into the vagina when it is worn and thus create a direct contact between the vagina and the absorbent hygiene product.

FIG. 5 shows in an appropriate view an absorbent structure 58 produced by extrusion having varying thickness d in the longitudinal direction of extrusion 44. Furthermore, the absorbent structure shown 58 has a varying width b in the longitudinal direction 44. The absorbent structure shown 58 would lend itself to the production of a diaper, whereby arcuate leg openings 60 are provided in the middle and in this area forming the crotch of the diaper an agglomeration of material is given by the greater thickness d provided there.

FIG. 6 shows schematically a suggested continuous extruded web 62 with varying width b in the longitudinal and extrusion direction 44. The broken lines 64 suggests the division of the continuous web by transverse cutting to create individual sections for the production of diapers.

Figure 8:
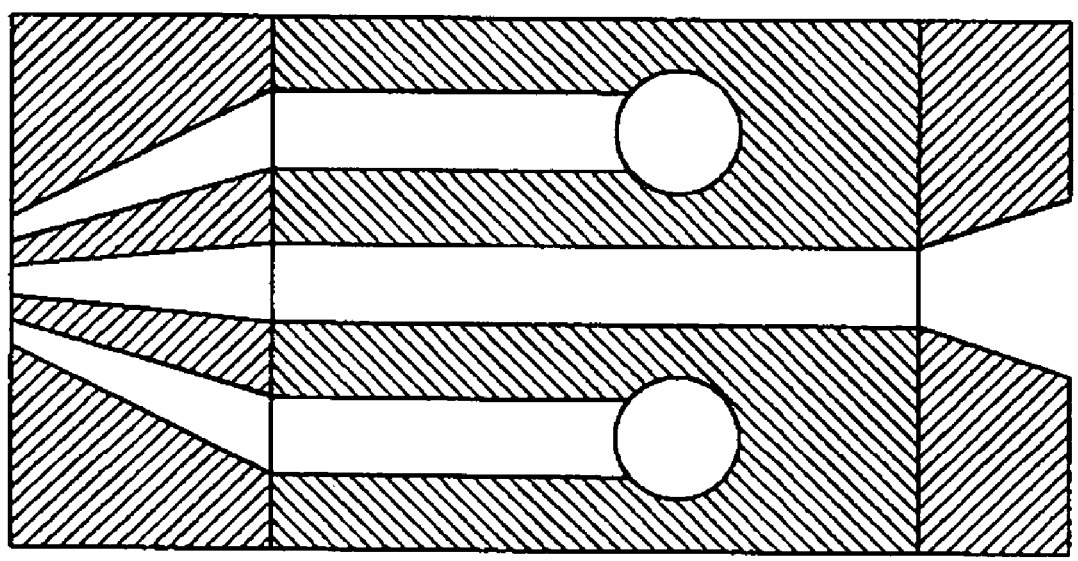
FIG. 8 shows a schematic representation of a coextrusion apparatus.

FIG. 7 shows a continuous extruded absorbent structure 66, which is produced by the coextrusion of three layers which is suitable for use in a hygiene article, in particular, a diaper. The structure comprises a first lower extruded film layer 68 of PE and/or PP. A middle extruded layer 70 formed on the basis of superabsorbent polymer materials with a moisture content of at least 1% by weight, which from its composition can correspond to the layer described in connection with FIG. 7, is identified with the reference numeral 70. A surface layer 72 on a polyester fiber (PES) base free firstly of superabsorbent polymer materials and secondly of polyethylene and/or polypropylene (PE/PP) is furnished on its upper side. All three layers 68, 70, 72 are produced in a coextrusion apparatus as shown schematically in FIG. 8, whereby to produce layer 72 a blowing agent under overpressure was used to create an open-pore foamed structure through expansion and evaporation of the blowing agent. The structure 66 is configured in cross-section in accordance with FIG. 3; it has lateral upwardly extending wall areas 46 running in the longitudinal direction 44, which can act as a leakage barrier in a hygiene article and perform the function of gatherings normally formed on the basis of nonwoven materials. The agglomeration of material from a greater thickness of the absorbent layer 70 in a center area 48 makes available a greater fluid absorption capacity from greater quantities of superabsorbent polymer materials. The upper layer 72 facing the body functions as a fluid distribution and intermediate retention layer. This means it captures a great volume of fluid through its greater volume of pores when suddenly impacted by fluid, then distributes this fluid with a time-delay in the direction of its thickness, but also in a horizontal direction, and releases it to the retention layer 70 located below it.

The fluid retention capability of an inventive extruded absorbent structure with a proportion of least 70% by weight of superabsorbent polymer materials is determined by the centrifuge test to be described in what follows by giving its retention value. The absorbent structure to be tested is weighed in its dry state to determine its mass in grams. A plurality of specimens are immersed completely for 30 minutes in a 1-percent aqueous solution of sodium chloride of demineralized water as the test solution and then centrifuged for 4 minutes at 276 times the force of gravity. Then the specimens are weighed again to determine their mass including the fluid bound in them. The mass of the absorbed or bound fluid is therefore the difference between the mass determined after centrifuging and the dry mass of each of the specimens. If this difference $m_{fl}$ is divided by the dry mass $m_{dry}$, the result is the retention value $g_{fl}/g_{dry}$ in the unit.

What is claimed is:

1. Method for producing an absorbent structure, comprising the following steps:

introducing a thermoplastic polymer, and a superabsorbent particulate polymer material into a closed system extrusion apparatus wherein the superabsorbent particulate polymer material has a moisture content of at least 0.5% by weight; melting the thermoplastic polymer material at temperatures below a melting or degradation temperature of the superabsorbent particulate polymer material at an elevated pressure to produce a mixture; extruding the mixture, whereby the moisture in the superabsorbent particulate polymer material evaporates as pressure is reduced and results in foaming of the melted thermoplastic polymer, which bonds the particulate superabsorbent polymer material together with the thermoplastic polymer to create a matrix composed of foamed thermoplastic polymer surrounding superabsorbent particulate polymer material;

wherein the percentage by weight of the superabsorbent particulate polymer material is at least 70% by weight of the admixture introduced into the extrusion apparatus; wherein the method is integrated into a production process for hygiene articles and therein the absorbent structure is extruded directly inside machinery for the high-speed production of hygiene articles, wherein inside the high-speed production machinery a triple-layer absorbent core is formed by coextrusion of the layers, whereby the absorbent core comprises the absorbent structure as absorbent core layer and a fluid distribution and intermediate retention layer on the body-facing side of the core layer and wherein the third layer is a fluid-impervious film which is located on the side of the absorbent core layer facing away from the body.

2. Method in accordance with claim 1, wherein the thermoplastic polymer becomes molten at temperatures of 80 to 200 degrees Celsius.

3. Method in accordance with claim 2 further comprising the step of introducing fibers as an additive into the extrusion apparatus, the fibers having a melting temperature less than the temperature at which the thermoplastic polymer is melted in the extrusion apparatus.

4. Method in accordance with claim 1, wherein a surfactant substance is introduced as an additive into the extrusion apparatus.

5. Method of claim 1, wherein the step of introducing superabsorbent particle polymer material further comprises the step of introducing the superabsorbent particle polymer material having a moisture content of at least 1% by weight.

6. Method of claim 1, wherein the step of introducing superabsorbent particle polymer material further comprises the step of introducing superabsorbent particulate polymer having a moisture content of at least 4% by weight.

7. Method for producing an absorbent structure in accordance with claim 1, wherein the resulting structure has a retention capacity of at least 10 g/g.

8. Method for producing an absorbent structure in accordance with claim 1, wherein the percentage by weight of the thermoplastic polymer is at least one of less than 30% by weight of the absorbent structure, less than 20% of the absorbent structure, or less than 10% by weight of the absorbent structure.

9. Method of producing an absorbent structure in accordance with claim 1, wherein the degree of foaming is at least 20%.

10. Method of producing an absorbent structure in accordance with claim 3, wherein the resulting structure comprises 3%-20% by weight, specifically 5%-10% by weight, fibers as additives.

* * * * *